US009844556B2

(12) United States Patent
Honjo et al.

(10) Patent No.: US 9,844,556 B2
(45) Date of Patent: Dec. 19, 2017

(54) PREVENTIVE/THERAPEUTIC METHOD AND PREVENTIVE/THERAPEUTIC AGENT FOR COMPLICATIONS AFTER CATARACT SURGERY

(71) Applicants: Megumi Honjo, Tokyo (JP); KOWA COMPANY, LTD., Nagoya-shi, Aichi (JP)

(72) Inventors: Megumi Honjo, Tokyo (JP); Eiji Wato, Fuji (JP); Masayuki Ohta, Higashimurayama (JP)

(73) Assignees: MEGUMI HONJO, Tokyo (JP); KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 15/079,934

(22) Filed: Mar. 24, 2016

(65) Prior Publication Data

US 2017/0020887 A1    Jan. 26, 2017

(30) Foreign Application Priority Data

Mar. 25, 2015   (JP) ................ 2015-063318
Sep. 25, 2015   (JP) ................ 2015-187759

(51) Int. Cl.
*A61K 31/551*   (2006.01)
*A61K 9/00*     (2006.01)
*A61K 9/08*     (2006.01)

(52) U.S. Cl.
CPC .......... *A61K 31/551* (2013.01); *A61K 9/0048* (2013.01); *A61K 9/08* (2013.01)

(58) Field of Classification Search
None
See application file for complete search history.

(56) References Cited

U.S. PATENT DOCUMENTS

| 5,767,079 | A  | 6/1998 | Glaser et al. |
| 5,925,617 | A  | 7/1999 | Kiritoshi et al. |
| 6,186,148 | B1 | 2/2001 | Okada |
| 6,376,543 | B1 | 4/2002 | Isaji et al. |
| 6,673,812 | B1 | 1/2004 | Azuma et al. |
| 2004/0047900 | A1 | 3/2004 | Allan |
| 2011/0130388 | A1 | 6/2011 | Ikuno et al. |

FOREIGN PATENT DOCUMENTS

| JP | 8-502033 A | 3/1996 |
| JP | 8-175984 A | 7/1996 |
| JP | 9-235239 A | 9/1997 |
| JP | 9-291040 A | 11/1997 |
| JP | 10-17487 A | 1/1998 |
| JP | 2002-502821 A | 1/2002 |
| JP | 2004-518649 A | 6/2004 |
| WO | 98/16214 A1 | 4/1998 |
| WO | 00/09162 A1 | 2/2000 |
| WO | 2010/010702 A1 | 1/2010 |

OTHER PUBLICATIONS

Kessel Ophthalmology 2014 vol. 121 pp. 1915-1924.*
Tanihara, H. et al Acta Ophthalmologica 2015 vol. 93 pp. e254-e260.*
Tian et al., "Effect of H-7 on Secondary Cataract After Phacoemulsification in the Live Rabbit Eye", Journal of Ocular Pharmacology and Therapeutics, Nov. 6, 2010, vol. 26, pp. 533-539, cited in Specification (8 pages).
Hirayama et al., "The Involvement of the Rho-Kinase Pathway and Its Regulation in Cytokine-Induced Collagen Gel Contraction by Hyalocytes", Investigative Ophthalmology & Visual Science, Nov. 2004, vol. 45, No. 11, pp. 3896-3903, cited in Specification (8 pages).
Meyer-Ter-Vebn et al., "Contractility as a Prerequisite for TGF-β-Induced Myofibroblast Transdifferentiation in Human Tenon Fibroblasts", Investigative Ophthalmology & Visual Science, Nov. 2006, vol. 47, No. 11, pp. 4895-4904, cited in Specification (10 pages).
Honjo et al., "Potential Role of Rho-Associated Protein Kinase Inhibitor Y-27632 in Glaucoma Filtration Surgery", Investigative Ophthalmology & Visual Science, Dec. 2007, vol. 48, No. 12, pp. 5549-5557, cited in Specification (9 pages).
Kita et al., "Role of TGF-β in proliferative vitreoretinal diseases and Rock as a therapeutic target", PNAS, Nov. 11, 2008, vol. 105, No. 45, pp. 17504-17509, cited in Specification (6 pages).
"Pharmaceutical Interview Form "GLANATEC® Ophthalmic Solution 0.4%"", prepared in accordance with the 2013 guidelines for preparation of the Interview Form by the Japanese Society of Hospital Pharmacists, published by Kowa Co., Japan, Sep. 26, 2014, Revised Jan. 2015, 74 pges.
"GLANATEC® Ophthalmic Solution 0.4%" (Package Insert), Kowa Co., Japan, Sep. 26, 2014, Revised Dec. 2014, 6 pages.
"Report of the Deliberation Results", Pharmaceutical and Food Safety Bureau, Japan, dated Sep. 11, 2014, Published Oct. 10, 2014, 62 pages.
"Summary of Toxicity Studies GLANATEC Ophthalmic Solution 0.4 %", Kowa Co., Japan, Sep. 26, 2014, Published Nov. 19, 2014, 154 pages.

* cited by examiner

*Primary Examiner* — Heidi Reese
(74) *Attorney, Agent, or Firm* — Westerman, Hattori, Daniels & Adrian, LLP (57) ABSTRACT

The present invention provides a method for the prevention and treatment of complications after cataract surgery such as secondary cataract and anterior capsule contraction that occur after cataract operation.
The present invention relates to a preventive/therapeutic method comprising administering to a subject a medicine containing 4-fluoro-5-{[(2S)-2-methyl-1,4-diazepan-1-yl]sulfonyl}isoquinoline (Ripasudil) or a salt thereof, or a solvate thereof as an active ingredient.

6 Claims, 6 Drawing Sheets

[FIG. 1A]

Control    Ripasudil-10μM    Ripasudil-100μM    Ripasudil-1mM

[FIG. 1B]

Control    Ripasudil-100μM    Ripasudil-1mM

[FIG. 2A]

Control    Y-27632-1mM

[FIG. 2B]

Control    Y-27632-1mM

[FIG. 3A]

Control          CD-2μM

[FIG. 3B]

Control          CD-2μM

[FIG. 4]

| Treatment Concentration | Treatment times with Ripasudil or medium(control) to HLEpiC | | |
|---|---|---|---|
| | Pre | 24hr | 48hr |
| Control (Medium) | | | |
| Ripasudil 10 μM | | | |
| Ripasudil 100 μM | | | |
| Ripasudil 1 mM | | | |

[FIG. 5]

| Treatment Concentration | Treatment times with Y-27632 or medium(control) to HLEpiC | | |
|---|---|---|---|
| | Pre | 24hr | 48hr |
| Control (Medium) | | | |
| Y-27632 1mM | | | |

[FIG. 6]

| Treatment Concentration | Treatment times with Cytochalasin D or medium(control) to HLEpiC | | |
|---|---|---|---|
| | Pre | 24hr | 48hr |
| Control (Medium) | | | |
| Cytochalasin D 2 μM | | | |

[FIG. 7]

| Treatment Concentration | Observation times after removal of Ripasudil or medium(control) | | | |
|---|---|---|---|---|
| | Pre | 24hr | 48hr | 116hr |
| Control | | | | |
| Ripasudil 100 μM | | | | |
| Ripasudil 1mM | | | | |

PREVENTIVE/THERAPEUTIC METHOD AND PREVENTIVE/THERAPEUTIC AGENT FOR COMPLICATIONS AFTER CATARACT SURGERY

BACKGROUND

Technical Field

The present invention relates to a novel medicine useful for the prevention and treatment of complications after cataract surgery such as secondary cataract and anterior capsule contraction.

Related Art

The crystalline lens refracts light entering into the eye to form an image on the retina and is responsible for the image formation system with the cornea. The anterior surface touches the posterior iris surface through the aqueous humor in the posterior chamber and the posterior surface touches the vitreous body. The crystalline lens is a transparent avascular tissue, and surrounded with a transparent thin membrane called the lens capsule. The anterior surface of the lens capsule is called the anterior capsule, the posterior surface is called the posterior capsule, and the part of the disc edge is called the equator. The zonule of Zinn connects the equator, and is involved in regulating the thickness of the crystalline lens.

The lens epithelial cells line the inside of the lens capsule, and cell division is observed near the equator (epithelial cells in the proliferative zone). The epithelial cells in the equator take the form of an elongated rectangle to differentiate into fiber cells, which are extended to the posterior capsule, transferred towards the central part of the crystalline lens, compressed to the central part of the crystalline lens and dehydrated to form the nucleus of the crystalline lens. As described above, the posterior capsule is fibers, and different from the anterior capsule in this respect. In general, the lens epithelial cells are moderately proliferated, and it is believed that the crystalline lens become heavier and thicker with increasing age.

In addition, spinelike processes, ridge processes and gap junctions exist between fiber cells into which epithelial cells are differentiated, and when there are abnormalities in epithelial cell division and abnormalities in extension to the posterior capsule, opacification due to lens fibers can occur.

Cataracts are caused by lens opacity, and, because incident light is scattered by lens opacity, symptoms such as blurred vision, double vision and intolerance of light emerge, and visual acuity is reduced with progression and cannot be corrected even with eyeglasses. The causes of cataract include congenital conditions, external injuries, atopy, drugs, radiation and the like; however, most of the cataracts are caused by aging, which are generally called senile cataract (age-related cataract) and are believed to be mainly caused by the progression of cortical opacity (cortical cataract) and nuclear sclerosis (nuclear cataract). The surface of light which passes through the crystalline lens varies depending on the size of the pupil, and thus when opacification occurs in the site through which light does not pass, there are almost no subjective symptoms. When observing the crystalline lens in a pupil dilation test (mydriasis test), however, cataracts are detected in people in their forties in the earlier cases, and in the majority of people in their eighties.

In the very early stage of cataract, the progression can be delayed with an ophthalmic preparation in some cases; however, the crystalline lens in which opacification has occurred once cannot be recovered, and for advanced cataract, a method in which the nucleus and cortex of the opaque crystalline lens are removed by a surgical operation (extracapsular lens extraction) and an intraocular lens is inserted is generally carried out. An example thereof is a method in which the anterior surface of the lens capsule (anterior capsule) is incised in a circular manner, the contents in the capsule are fragmented with ultrasonic and sucked, and an intraocular lens is inserted into the remaining capsule, and inserting an intraocular lens becomes easy by leaving the capsule.

This operation hardly causes pain, ends in a relatively short time, and restores visual acuity by inserting an intraocular lens, and thus has been used as a method for treating cataract. It is also said that the disease rate of senile cataract is 60 to 70% in people in their sixties and further almost 100% in people in their eighties or older. In the present situation in which aging society progresses, the importance of the treatment of cataract has increasingly risen, and operation methods and intraocular lenses have been improved.

After a period of time after the operation, however, the crystalline lens can become turbid again by, for example, the proliferation and transfer to the posterior capsule of the lens cells remaining in the capsule. When the opacification progresses, visual function declines and cataract symptoms emerge in some cases. This is called "secondary cataract", and the incidence rate is reported to be above 19%. However, a complete method for preventing and treating secondary cataract has not been established until now.

As the onset mechanism of secondary cataract, it is mainly believed that posterior capsule opacification (PCO) arises by the migration to the posterior capsule and proliferation of the remaining lens epithelial cells which have not been completely removed by extracapsular lens extraction, or Soemmerring's ring cataract, which has a ring-shaped opacity, and Elschnig's pearls, which have a pearl-like opacity, are formed by, for example, the abnormal proliferation of lens epithelial cells remaining in the equator. It is impossible to completely remove lens epithelial cells in a cataract operation and it is difficult to completely prevent secondary cataract. It is demanded that a medicine for the prevention and treatment of secondary cataract be developed.

In addition, the window of the lens capsule obtained by incising the anterior surface of the lens capsule (anterior capsule) in a circular manner in the cataract operation described above becomes small after the operation in some cases. Such symptom is called "anterior capsule contraction". This occurs because the lens cells remaining around the incised window are changed to fibrous cells by for example an inflammatory reaction and proliferated to narrow the incised circular window as a purse. This does not normally affect visual function in most cases; however, when the size of the window is increased to cover the central part of the pupil, light is difficult to enter into the eyes, which causes a declined visual function. The "anterior capsule contraction" is also a disease occurring after a cataract operation, and an effective method for the prevention and treatment thereof has not been developed as is the case with secondary cataract, and it is demanded that a medicine for the prevention and treatment of anterior capsule contraction be developed.

Various substances have been reported as secondary cataract inhibitors. It has been for example reported that N-(3, 4-dimethoxycinnamoyl)anthranilic acid (general name: Tranilast) known as a therapeutic agent for allergic diseases such as bronchial asthma and allergic rhinitis is used (see WO 98/16214 A), ethylenediaminetetraacetic acid is used as a sustained release preparation (see JP 8-175984 A), transforming growth factor-β (TGF-β) is used (see JP 8-502033 W), a sustained release preparation including, e.g. a 2-piperazinone derivative having a nonpeptidic inhibitory activity on cell adhesion and a polymer is used (see JP 9-235239 A), a polypeptide having an inhibitory activity on cell adhesion and a lactic acid-glycolic acid polymer are used (see JP 9-291040 A), a peptide such as Arg-Gly-Asp is used (see JP 10-17487 A), a focal adhesion modulating substance to regulate adhesion between lens epithelial cells and the lens capsule, e.g. an enzyme precursor of serine protease, is used (see JP 2002-502821 W), a polymer to which a cell death receptor ligand such as Fas ligand is fixed is used (see JP 2004-518649 W), and the like.

It has been also reported that H-7, a kind of serine threonine kinase inhibitor, is effective for resolving Soemmerring's ring, but ineffective for posterior capsule opacification (PCO) (see Baohe Tian, et al., J. Ocular Pharm. Ther., 26(6), 2010, 533-539).

In the meantime, it has been reported that Rho kinase (Rho-Associated, Coiled-Coil Containing Protein Kinase: ROCK) inhibitors (hereinafter, also referred to as ROCK inhibitors) such as fasudil and Y-27632 are used for the treatment of for example glaucoma (see e.g. WO 00/09162 A), and it has been also reported that the ROCK inhibitors are useful as a preventive or therapeutic agent for axial myopia (see WO 2010/010702 A).

It has been also reported that ROCK inhibitors, HF (Hydroxyfasudil) and Y-27632, inhibited contraction induced by cytokines such as PDGF-BB and TGF-β2 in bovine lens cells (see Kumiko Hirayama, et al., IOVS, 45(11), 2004, 3896-3903), ROCK inhibitors, Y-27632, HA-1077, H-1152 and ML-7, inhibit the transdifferentiation and contraction of myofibroblasts induced by TGF-β, which are useful for postoperative scars of glaucoma filtration surgery (see Tobias Meyer-ter-Vehn, et al., IOVS, 47(11), 2006, 4895-4904), a ROCK inhibitor, Y-27632, does not promote proliferation but promotes adhesive properties, and is useful as an anti-scar agent after glaucoma filtration surgery (see Megumi Honjo, et al., IOVS, 48(12), 2007, 5549-5557), and a ROCK inhibitor, fasudil, inhibits hyalocyte-containing collagen gel contraction and is useful for the treatment of vitreoretinopathy (see Takeshi Kita, et al., PNAS, 105(45), 2008, 17504-17509).

It has not been reported, however, that ROCK inhibitors are useful for the prevention and treatment of complications after cataract surgery such as secondary cataract and anterior capsule contraction.

SUMMARY

The present invention provides a novel medicine for the prevention and treatment of complications after cataract surgery such as secondary cataract and anterior capsule contraction, which develop after a cataract operation, particularly extracapsular lens extraction to remove the opaque lens by a surgical operation.

The present invention also provides a novel medicine as an actin stress fiber formation inhibitor, particularly as an actin stress fiber formation inhibitor for lens epithelial cells after a cataract surgical operation.

The present invention also provides a novel medicine as a cell migration inhibitor, particularly as a cell migration inhibitor for lens epithelial cells after a cataract surgical operation.

The present invention also provides a novel medicine as a cytostatic agent, particularly as a cytostatic agent for lens epithelial cells after a cataract surgical operation.

The present invention further provides a novel medicine as a collagen gel contraction inhibitor, particularly a collagen gel contraction inhibitor after a cataract surgical operation.

The present invention provides a method for the prevention and/or treatment of the above-mentioned various diseases using the medicines mentioned above.

The present inventors have investigated various actions of 4-fluoro-5-{[(2S)-2-methyl-1,4-diazepan-1-yl]sulfonyl}isoquinoline (hereinafter, also referred to as Ripasudil) represented by the following formula.

The therapeutic agent of glaucoma and ocular hypertension, containing ripasudil hydrochloride dihydrate as an active ingredient has already received manufacture and sales approval as the trade name "Glanatec" (registered trademark).

The present inventors have observed that the degeneration images of lens fibers accompanied by opacification are recognized in the sutures in the anterior part of the crystalline lens in the administration group, 13 week repeated ocular administration of RIPASUDIL ophthalmic solution 2.0% to rabbits (twice/day), and the administration group, 13 week repeated ocular administration of RIPASUDIL ophthalmic solution 4.0% to dogs (4 times/day). Such changes have been thought to be caused by reasons that the inhibition of actin stress fiber formation occurs by the ROCK inhibitory action of Ripasudil, and differentiation into lens fiber cells and extension and migration after that are inhibited.

In order to prove these, the present inventors examined these using human lens epithelial cells. As a result, an obvious decrease in actin stress fibers by ripasudil was recognized, but this change was reversible. The inhibition of cell migration was also confirmed, and this change was also reversible.

The same change was further recognized using Y-27632, which is known to have the ROCK inhibitory action, and thus the inhibitory action on actin stress fiber formation and the inhibitory action on cell migration by Ripasudil were determined to be actions based on the ROCK inhibitory action.

From the above, it turned out that Ripasudil had the inhibitory action on actin stress fiber formation and the inhibitory action on cell migration, which are reversible, in human lens epithelial cells, and differentiation into the lens fiber cells, and extension and migration after that were inhibited by the inhibition of actin stress fiber formation.

The present inventors further investigated an inhibitory action on human lens epithelial cell proliferation, an inhibitory action on fibroblast proliferation, and an inhibitory action on collagen gel contraction by Ripasudil. The results showed that Ripasudil also had a cytostatic action and an inhibitory action on collagen gel contraction.

As described above, Ripasudil not only has an inhibitory action on proliferation of the remaining lens epithelial cells, which have not been completely removed when the nucleus and cortex of the crystalline lens are extracted after an excision of the anterior capsule in cataract surgical operation, but also has an inhibitory action on differentiation, extension and migration of lens epithelial cells by the inhibition of actin stress fiber formation, and further has an inhibitory action on collagen contraction. Therefore, it turned out that Ripasudil was effective for the prevention and/or treatment of complications after cataract surgery such as secondary cataract and anterior capsule contraction.

That is, the present invention relates to a preventive/therapeutic agent for complications after cataract surgery such as secondary cataract and anterior capsule contraction, the preventive/therapeutic agent containing 4-fluoro-5-{[(2S)-2-methyl-1,4-diazepan-1-yl]sulfonyl}isoquinoline (Ripasudil) or a salt thereof, or a solvate thereof as an active ingredient.

The present invention also relates to an actin stress fiber formation inhibitor, containing Ripasudil or a salt, or a solvate thereof as an active ingredient, preferably an actin stress fiber formation inhibitor for lens epithelial cells, and more preferably an actin stress fiber formation inhibitor for lens epithelial cells after a cataract surgical operation.

The present invention also relates to a cell migration inhibitor, containing Ripasudil or a salt thereof, or a solvate thereof as an active ingredient, preferably a cell migration inhibitor for lens epithelial cells, and more preferably a cell migration inhibitor for lens epithelial cells after a cataract surgical operation.

The present invention also relates to a cytostatic agent, containing Ripasudil or a salt thereof, or a solvate thereof as an active ingredient, preferably a cytostatic agent for lens epithelial cells, and more preferably a cytostatic agent for lens epithelial cells after a cataract surgical operation.

The present invention further relates to a collagen gel contraction inhibitor, containing Ripasudil or a salt thereof, or a solvate thereof as an active ingredient, and preferably a collagen gel contraction inhibitor after a cataract surgical operation.

The present invention also relates to a method for preventing and/or treating complications after cataract surgery such as secondary cataract and/or anterior capsule contraction comprising administering to a subject therapeutically and/or preventively effective amount of Ripasudil or a salt thereof, or a solvate thereof.

According to the present invention, there can be provided a drug for the prevention and/or treatment of complications after cataract surgery such as secondary cataract and anterior capsule contraction. Ripasudil of the present invention or a salt thereof, or a solvate thereof has an inhibitory action on actin stress fiber formation and an inhibitory action on cell migration, which are reversible, and not only can be used, by using these properties, as an actin stress fiber formation inhibitor, preferably an actin stress fiber formation inhibitor for lens epithelial cells, and more preferably an actin stress fiber formation inhibitor for lens epithelial cells after a cataract surgical operation, also a cell migration inhibitor, preferably a cell migration inhibitor for lens epithelial cells, and more preferably a cell migration inhibitor for lens epithelial cells after a cataract surgical operation, also a cytostatic agent, preferably a cytostatic agent for lens epithelial cells, and more preferably a cytostatic agent for lens epithelial cells after a cataract surgical operation, and a collagen gel contraction inhibitor, and preferably a collagen gel contraction inhibitor after a cataract surgical operation, but also, from the above, is useful as a preventive/therapeutic agent for complications after cataract surgery such as secondary cataract and anterior capsule contraction.

The complications after cataract surgery such as secondary cataract and anterior capsule contraction occurring after a cataract operation disrupt the recovery of visual function after a surgical operation, and are serious diseases for patients. No drug effective in preventing or treating the diseases has, however, developed until now, and there has been only treatment by a laser. The present invention provides a novel drug, which is able to prevent and treat the diseases by an easy administration treatment such as ocular instillation.

Furthermore, there is apprehension about an increasing number of patients with senile cataract due to an aging society; however, the drug of the present invention is able to simply and effectively inhibit complications after cataract surgery such as secondary cataract and anterior capsule contraction occurring after a cataract operation, and the patients are able to have a cataract operation without anxiety.

DETAILED DESCRIPTION

An aspect of the present invention will be described in more detail as follows.

That is, the present invention is involved in the following inventions.

(1) A preventive/therapeutic agent for complications after cataract surgery such as secondary cataract and anterior capsule contraction, the preventive/therapeutic agent containing 4-fluoro-5-{[(2S)-2-methyl-1,4-diazepan-1-yl]sulfonyl}isoquinoline or a salt thereof, or a solvate thereof as an active ingredient.
(2) The preventive and/or therapeutic agent according to (1) above, wherein the solvate is a hydrate.
(3) The preventive/therapeutic agent according to (1) or (2) above, wherein the treatment is to block the progression of opacity or contraction of the lens capsule.
(4) The preventive/therapeutic agent according to any one of (1) to (3) above, wherein the preventive/therapeutic agent is administered from during a cataract operation or after a cataract operation.
(5) The preventive/therapeutic agent according to (4) above, wherein the cataract operation includes extracapsular lens extraction.
(6) A pharmaceutical composition for the prevention/treatment of complications after cataract surgery such as secondary cataract and anterior capsule contraction, the pharmaceutical composition containing Ripasudil or a salt thereof, or a solvate thereof, and a pharmaceutically acceptable carrier.
(7) The pharmaceutical composition according to (6) above, wherein the solvate is a hydrate.
(8) The pharmaceutical composition according to (6) or (7) above, wherein the treatment is to block the progression of opacity or contraction of the lens capsule.
(9) The pharmaceutical composition according to any one of (6) to (8) above, wherein the pharmaceutical composition for prevention/treatment is administered from during a cataract operation or after a cataract operation.
(10) The pharmaceutical composition according to (9) above, wherein the cataract operation includes extracapsular lens extraction.
(11) An ophthalmic preparation for the prevention/treatment of complications after cataract surgery such as secondary cataract and anterior capsule contraction, the ophthalmic preparation containing Ripasudil or a salt thereof, or a solvate thereof, and an acceptable carrier for ophthalmic preparations.
(12) The ophthalmic preparation according to (11) above, wherein the solvate is a hydrate.
(13) The ophthalmic preparation according to (11) or (12) above, wherein the treatment is to block the progression of opacity or contraction of the lens capsule.
(14) The ophthalmic preparation according to any one of (11) to (13) above, wherein the ophthalmic preparation for prevention/treatment is administered from during a cataract operation or after a cataract operation.
(15) The ophthalmic preparation according to (14) above, wherein the cataract operation includes extracapsular lens extraction.
(16) An actin stress fiber formation inhibitor, containing 4-fluoro-5-{[(2S)-2-methyl-1,4-diazepan-1-yl]sulfonyl}isoquinoline or a salt thereof, or a solvate thereof as an active ingredient.
(17) The actin stress fiber formation inhibitor according to (16) above, wherein the solvate is a hydrate.
(18) The actin stress fiber formation inhibitor according to (16) or (17) above, wherein the actin stress fiber formation inhibitor is an actin stress fiber formation inhibitor for lens epithelial cells.
(19) The actin stress fiber formation inhibitor according to any one of (16) to (18) above, wherein the actin stress fiber formation inhibitor is an actin stress fiber formation inhibitor for lens epithelial cells after a cataract surgical operation.
(20) The actin stress fiber formation inhibitor according to any one of (16) to (19) above, wherein the actin stress fiber formation inhibitor prevents lens opacity after a cataract surgical operation.
(21) The actin stress fiber formation inhibitor according to any one of (16) to (20) above, wherein the actin stress fiber formation inhibitor inhibits the morphogenesis of the crystalline lens after a cataract surgical operation.
(22) The actin stress fiber formation inhibitor according to any one of (16) to (21) above, wherein the actin stress fiber formation inhibitor is for the prevention/treatment of complications after cataract surgery such as secondary cataract and anterior capsule contraction.
(23) A cell migration inhibitor, containing 4-fluoro-5-{[(2S)-2-methyl-1,4-diazepan-1-yl]sulfonyl}isoquinoline or a salt thereof, or a solvate thereof as an active ingredient.
(24) The cell migration inhibitor according to (23) above, wherein the solvate is a hydrate.
(25) The cell migration inhibitor according to (23) or (24) above, wherein the cell migration inhibitor is a cell migration inhibitor for lens epithelial cells.
(26) The cell migration inhibitor according to any one of (23) to (25) above, wherein the cell migration inhibitor is a cell migration inhibitor for lens epithelial cells after a cataract surgical operation.
(27) The cell migration inhibitor according to any one of (23) to (26) above, wherein the cell migration inhibitor prevents lens opacity after a cataract surgical operation.
(28) The cell migration inhibitor according to any one of (23) to (27) above, wherein the cell migration inhibitor inhibits the morphogenesis of the crystalline lens after a cataract surgical operation.
(29) The cell migration inhibitor according to any one of (23) to (28) above, wherein the cell migration inhibitor is for the prevention/treatment of complications after cataract surgery such as secondary cataract and anterior capsule contraction.
(30) A cytostatic agent, containing 4-fluoro-5-{[(2S)-2-methyl-1,4-diazepan-1-yl]sulfonyl}isoquinoline or a salt thereof, or a solvate thereof as an active ingredient.
(31) The cytostatic agent according to (30) above, wherein the solvate is a hydrate.
(32) The cytostatic agent according to (30) or (31) above, wherein the cytostatic agent is a cytostatic agent for lens epithelial cells.
(33) The cytostatic agent according to any one of (30) to (32) above, wherein the cytostatic agent is a cytostatic agent for lens epithelial cells after a cataract surgical operation.

(34) The cytostatic agent according to any one of (30) to (33) above, wherein the cytostatic agent prevents lens opacity after a cataract surgical operation.
(35) The cytostatic agent according to any one of (30) to (34) above, wherein the cytostatic agent inhibits the morphogenesis of the crystalline lens after a cataract surgical operation.
(36) The cytostatic agent according to any one of (30) to (34) above, wherein the cytostatic agent is for the prevention/treatment of complications after cataract surgery such as secondary cataract and anterior capsule contraction.
(37) A collagen gel contraction inhibitor, containing 4-fluoro-5-{[(2S)-2-methyl-1,4-diazepan-1-yl]sulfonyl}isoquinoline or a salt thereof, or a solvate thereof as an active ingredient.
(38) The collagen gel contraction inhibitor according to (37) above, wherein the solvate is a hydrate.
(39) The collagen gel contraction inhibitor according to (37) or (38) above, wherein the collagen gel contraction inhibitor is a collagen gel contraction inhibitor after a cataract surgical operation.
(40) The collagen gel contraction inhibitor according to any one of (37) to (39) above, wherein the collagen gel contraction inhibitor prevents collagen gel contraction after a cataract surgical operation.
(41) The collagen gel contraction inhibitor according to any one of (37) to (40) above, wherein the collagen gel contraction inhibitor inhibits the morphogenesis of the crystalline lens after a cataract surgical operation.
(42) The collagen gel contraction inhibitor according to any one of (37) to (41) above, wherein the collagen gel contraction inhibitor is for the prevention/treatment of complications after cataract surgery such as secondary cataract and anterior capsule contraction.
(43) A method for preventing and/or treating complications after cataract surgery, comprising administering to a subject with or at a risk of complications after cataract surgery a medicine comprising therapeutically and/or preventively effective amount of 4-fluoro-5-{[(2S)-2-methyl-1,4-diazepan-1-yl]sulfonyl}isoquinoline or a salt thereof, or a solvate thereof as an active ingredient.
(44) The method according to the above (43) wherein the solvate is a hydrate.
(45) The method according to the above (43) and (44) wherein the complications after cataract surgery is secondary cataract.
(46) The method according to the above (43) and (44) wherein the complications after cataract surgery is anterior capsule contraction.
(47) The method according to the above (43) wherein the treatment is to block the progression of opacity or contraction of the lens capsule.
(48) The method according to the above (43) wherein the medicine is an ophthalmic solution.
(49) The method according to the above (43) wherein the cataract surgery includes extracapsular lens extraction.
(50) A method according to the above (43)-(49) wherein the method is for treatment.
(51) A method according to any one of the above (43)-(49) wherein the method is for prevention.
(52) A method according to the above (51) wherein the administration is made from during a cataract operation or after a cataract operation.
(53) A method for inhibiting formation of actin stress fiber using 4-fluoro-5-{[(2S)-2-methyl-1,4-diazepan-1-yl]sulfonyl}isoquinoline or a salt thereof, or a solvate thereof as an active ingredient.
(54) The method of the above (53) wherein the solvate is a hydrate.
(55) The method of the above (53) wherein the inhibition of formation of actin stress fiber is inhibition of formation of actin stress fiber in lens epithelial cells.
(56) The method of the above (53) wherein the inhibition of the formation of actin stress fiber prevents lens opacity after cataract surgical operation.
(57) The method of the above (53) wherein the inhibition of the formation of actin stress fiber inhibits the morphogenesis of the crystalline lens after cataract surgical operation.
(58) A method for inhibition of cell migration using 4-fluoro-5-{[(2S)-2-methyl-1,4-diazepan-1-yl]sulfonyl}isoquinoline or a salt thereof, or a solvate thereof as an active ingredient.
(59) The method according to the above (58) wherein the solvate is a hydrate.
(60) The method according to the above (58) wherein the inhibition of cell migration is the inhibition of cell migration in lens epithelial cells.
(61) The method according to the above (58) wherein the inhibition of cell migration is the inhibition of cell migration in lens epithelial cells after cataract surgical operation.
(62) The method according to the above (58) wherein the inhibition of cell migration prevents lens opacity after cataract surgical operation.
(63) The method according to the above (58) wherein the inhibition of cell migration inhibits the morphogenesis of the crystalline lens after cataract surgical operation.
(64) A method for inhibition of cell proliferation using 4-fluoro-5-{[(2S)-2-methyl-1,4-diazepan-1-yl]sulfonyl}isoquinoline or a salt thereof, or a solvate thereof as an active ingredient.
(65) A method according to the above (64) wherein the solvate is a hydrate.
(66) A method according to the above (64) wherein the inhibition of cell proliferation is inhibition of proliferation in lens epithelial cells.
(67) A method according to the above (64) wherein the inhibition of cell proliferation is inhibition of proliferation in lens epithelial cells after cataract surgical operation.
(68) A method according to the above (64) wherein inhibition of cell proliferation prevents lens opacity after cataract surgical operation.
(69) A method according to the above (64) wherein inhibition of cell proliferation is inhibition of the morphogenesis of the crystalline lens after cataract surgical operation.
(70) A method for inhibition of collagen gel contraction using 4-fluoro-5-{[(2S)-2-methyl-1,4-diazepan-1-yl]sulfonyl}isoquinoline or a salt thereof, or a solvate thereof as an active ingredient.
(71) A method according to the above (70) wherein the solvate is a hydrate.
(72) A method according to the above (70) wherein the inhibition of collagen gel contraction is inhibition of collagen gel contraction after cataract surgical operation.
(73) A method according to the above (70) wherein the inhibition of collagen gel contraction prevents collagen gel contraction after cataract surgical operation.
(74) A method according to the above (70) wherein the inhibition of collagen gel contraction is inhibition of the morphogenesis of the crystalline lens after cataract surgical operation.

It is known that secondary cataract develops due to proliferation, differentiation into fiber cells, extension and migration of lens epithelial cell after a cataract surgical operation. That is, it is known that the morphogenesis of the crystalline lens by lens epithelial cells after a cataract surgical operation causes opacity.

It has been also reported that the formation of actin stress fibers is important for the differentiation, extension and migration of lens fiber cells required for the morphogenesis of the crystalline lens (Rao, P. V. and Maddala, R. (2006): Semin. Cell. Dev. Biol., 17(6), 698-711).

Ripasudil of the present invention inhibits differentiation, extension and migration of the lens fiber cells by inhibiting the formation of actin stress fibers, and inhibits the morphogenesis of the crystalline lens. This means to be able to inhibit the differentiation, extension and migration of the lens fiber cells of the lens epithelial cells remaining after a cataract surgical operation, which is a useful property in the prevention/treatment of secondary cataract.

Further, Ripasudil of the present invention inhibits lens epithelial cell proliferation by inhibiting cell proliferation, which is a useful property in the prevention/treatment of secondary cataract.

Similarly, Ripasudil of the present invention also shows an inhibitory action on actin stress fiber formation and further an inhibitory action on collagen gel contraction, and thus also shows the possibility of being able to prevent and treat even anterior capsule contraction after a cataract surgical operation.

Ripasudil used in the present invention is a compound having a therapeutic agent for brain blood vessel, substance P antagonism, leukotriene D4 antagonism and the ROCK inhibitory action, and can be produced by a known method such as a method described in WO 99/20620 A.

Examples of salts of Ripasudil include salts of inorganic acids such as hydrochloric acid, sulfuric acid, nitric acid, hydrofluoric acid and hydrobromic acid, or salts with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid, and a hydrochloride is especially preferred.

Ripasudil or a salt thereof can exist not only in the nonsolvated form but also as a hydrate or a solvate. A hydrate is preferred; however, the present invention includes all crystal forms and hydrates or solvates.

Ripasudil or a salt thereof, or a solvate thereof has, as described in examples mentioned below, an inhibitory action on actin stress fiber formation, an inhibitory action on cell migration, a cytostatic action, and an inhibitory action on collagen contraction and the like, and is useful as a drug for the prevention and/or treatment of posterior capsule opacification, Soemmerring's ring cataract, the formation of Elschnig's pearls, complications after cataract surgery such as secondary cataract and anterior capsule contraction, and a decline in visual acuity and visual function due to the above.

In the present invention, "after cataract surgery" means after the treatment of cataract such as extracapsular lens extraction and after a surgical operation to improve visual function due to cataract. In the present invention, "after cataract surgery" is also referred to as "after a cataract operation" or "after a cataract surgical operation".

In the present invention, "complications after cataract surgery" include diseases accompanied by various symptoms which develop or can develop after the treatment of cataract such as extracapsular lens extraction and a surgical operation to improve visual function due to cataract, more specifically, diseases which develop or can develop due to, for example, the proliferation, differentiation, extension and migration of the lens fiber cells by lens epithelial cells which have not been completely removed by the above surgical operation. Typical examples of complications after cataract surgery include secondary cataract, anterior capsule contraction and the like.

In the present invention, "prevention/treatment" means prevention and/or treatment. The treatment herein includes the inhibition of the progression of opacity or contraction of the lens capsule. In addition, the prevention is not necessarily supposed to develop the diseases, and also includes inhibiting the possibility of developing the diseases. The prevention in the present invention further includes, when the nucleus and cortex of the crystalline lens are extracted after excising the anterior capsule in a cataract surgery, immediate administration after excising the anterior capsule in order to inhibit proliferation, differentiation, extension and migration of the remaining lens epithelial cells which have not been completely removed.

When formulations are produced from Ripasudil or a salt thereof, or a solvate thereof, the formulations can be prepared in accordance with known methods. The formulations of Ripasudil or a salt thereof, or a solvate thereof, for example, can be prepared by reference to e.g. the formulation examples described in International Publication (e.g. WO 00/09162, WO 97/23222).

When the formulations of Ripasudil or a salt thereof, or a solvate thereof are prepared, the formulations can be prepared in accordance with known methods. An ophthalmic solution, for example, can be prepared by using an isotonic agent, a buffer, a surface active agent, a preservative and the like as needed. Its pH is only required to be in an acceptable range for ophthalmic formulations and is preferably in a range of pH from 4 to 8.

The pharmaceutical formulation of the present invention is preferably used as an ophthalmic formulation, and such ophthalmic formulation can be any of an aqueous ophthalmic solution, a nonaqueous ophthalmic solution, an ophthalmic suspension, an ophthalmic emulsion, an ophthalmic ointment and the like. By art known (formulation) methods, such formulations can be produced as compositions suitable for administration forms by mixing a pharmaceutically acceptable carrier, for example in the case of an ophthalmic solution, an acceptable carrier for ophthalmic preparations, and for example an isotonic agent, a chelating agent, a stabilizer, a pH regulator, a preservative, an antioxidant, a solubilizing agent and a thickening agent as needed.

The active ingredient of the present invention has efficacy even by ocular administration, and can be used as an ophthalmic preparation. The ophthalmic preparation of the present invention contains the active ingredient of the present invention, Ripasudil or a salt thereof, or a solvate thereof, and an acceptable carrier for ophthalmic preparations.

When an ophthalmic solution is prepared, it can be prepared, for example, by dissolving or suspending desired ingredients described above in an aqueous solvent such as sterile purified water or a physiological saline solution, or a nonaqueous solvent, for example, vegetable oils such as cottonseed oil, soybean oil, sesame oil and peanut oil, adjusting the obtained mixture to a predetermined osmotic pressure and carrying out sterilization treatment such as filtration sterilization. When an ophthalmic ointment is prepared, various ingredients described above and further an ointment base can be contained therein. The above ointment bases are not particularly limited, and preferably include oily bases such as vaseline, liquid paraffin and polyethylene; emulsion bases in which an oil phase and an aqueous phase are emulsified by e.g. a surface active agent; water-soluble bases including hydroxypropyl methylcellulose, carboxymethyl cellulose, polyethylene glycol and the like; and the like.

When Ripasudil or a salt thereof, or a solvate thereof is used for the prevention and/or treatment of complications after cataract surgery such as secondary cataract and anterior capsule contraction, the dose varies depending on body weight, age, gender and symptoms of patients, administration forms, frequency of administration and the like, and includes normally 0.025 to 10000 μg daily, preferably 0.025 to 2000 μg, more preferably 0.1 to 2000 μg and further 0.025 to 200 μg to adults as (S)-(−)-1-(4-fluoro-5-isoquinolinesulfonyl)-2-methyl-1,4-homopiperazine or a salt thereof, or a solvate thereof.

In addition, the frequency of administration is not particularly limited, and a formulation is preferably administered once or in divided doses, and when using a liquid ophthalmic solution, a drop to a few drops can be applied once.

The present invention will now be described in more detail by way of examples thereof. It should be noted, however, that the present invention is not limited to these examples.

Example 1

Inhibitory Action on Actin Stress Fiber Formation:

Human lens epithelial cells (HLEpiC (ScienCell Research Laboratories)) were diluted with a medium (Epithelial Cell Medium (ScienCell Research Laboratories)), dispensed to each well of Poly-L-lysine (ScienCell Research Laboratories) coated Imaging Chamber CG at 100 μL/well (about 5000 cells/cm$^2$), and cultured in a carbon dioxide incubator (37° C., 5% $CO_2$) until about 50% confluent. The medium was removed with vacuum suction and a test substance, a positive control, a comparative control, or the medium (control) at each concentration given below was added to each well at 300 μL/well:

Test substance: Ripasudil with a concentration of 10 μM, 100 μM or 1 mM,

Positive control: Cytochalasin D with a concentration of 2 μM,

Comparative control: Y-27632 with a concentration of 1 mM, and

Control: only medium.

These were treated in a carbon dioxide incubator (37° C., 5% $CO_2$) for about an hour, and then washed once with the medium. 4% Paraformaldehyde Phosphate Buffer Solution (Wako Pure Chemical Industries, Ltd.) (hereinafter, referred to as a fixative solution) was added at 300 μL/well, and fixation was carried out at room temperature for 2 minutes. After washing with the medium, 0.5% Triton X-100 (Roche Diagnostics K.K.) was added at 300 μL/well, and penetrated at room temperature for 2 minutes. After washing with the medium, the fixative solution was added at 300 μL/well, and fixation was carried out at room temperature for 20 minutes.

Separately, 25 μL of 14 μM Actin-Stain™ 555 phalloidin (Cytoskeleton, Inc.) (hereinafter, referred to as Phalloidin) was added to 3475 μL of 10 mM phosphate buffered saline (Wako Pure Chemical Industries, Ltd.) to produce 100 nM Phalloidin.

This 100 nM Phalloidin was added to each well washed with the medium at 200 μL/well, and staining was carried out at room temperature in a dark place for about 60 minutes.

After washing with the medium, the chamber was removed, and VECTASHIELD Mounting Medium with DAPI (Vector Laboratories, Inc.) was dropped onto a cover glass with a few drops. A slide glass was placed thereon and this was left to stand at room temperature in a dark place for 30 minutes or more, and adhesion and nuclear staining were carried out and then observed by a confocal laser scanning microscope.

Figure 1A:
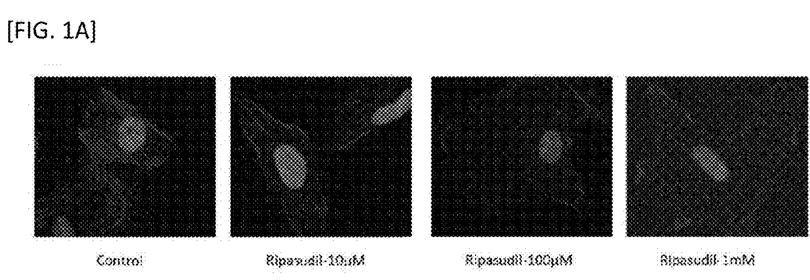
FIG. 1A is color photographs to observe the inhibitory action of Ripasudil of the present invention on actin stress fiber formation of lens epithelial cells (HLEpiC)
Figure 2A:
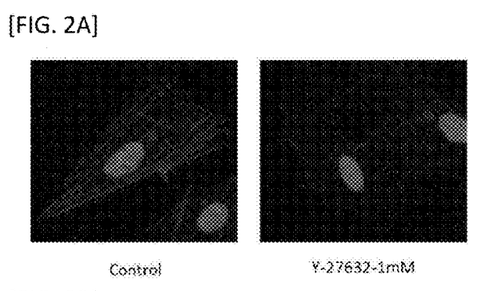
FIG. 2A is color photographs to observe the inhibitory action of Y-27632 used as a comparative control on actin stress fiber formation of HLEpiC.
Figure 3A:
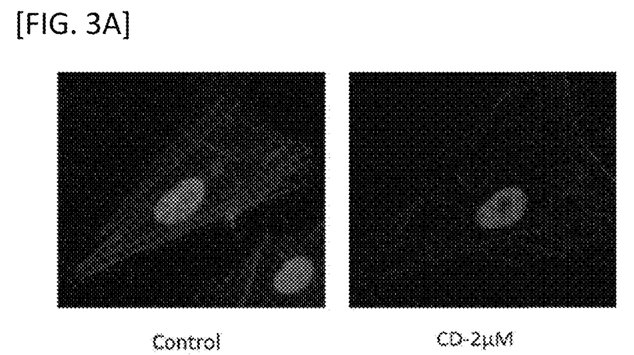
FIG. 3A is color photographs to observe the inhibitory action of Cytochalasin D (hereinafter, also referred to as CD) used as a positive control on actin stress fiber formation.

As the observation results, the test substance, Ripasudil, and the control are shown in FIG. 1A, the comparative control, Y-27632, and the control are shown in in FIG. 2A, and the positive control and the control are in FIG. 3A using respective color photographs. The actin stress fibers are colored in red in the color photographs.

It is found that the actin stress fibers slightly disappear in the test substance, Ripasudil 10 μM, and the actin stress fibers significantly disappear in 100 μM and 1 mM (see FIG. 1A). Similarly, the actin stress fibers also disappear in the comparative control, Y-27632 (see FIG. 2A). It is further found that the actin stress fibers significantly disappear in the positive control, CD (see FIG. 3A).

This showed that Ripasudil of the present invention had an inhibitory action on actin stress fiber formation.

Example 2

Reversibility of Inhibition of Actin Stress Fiber Formation:

After removal of the test substance, positive control or comparative control in Example 1, the cells were recultured for about another 24 hours, treated in accordance with the operation in Example 1, and then observed by a confocal laser scanning microscope in the same manner as in Example 1 to observe the reversibility of actin stress fibers.

Figure 1B:
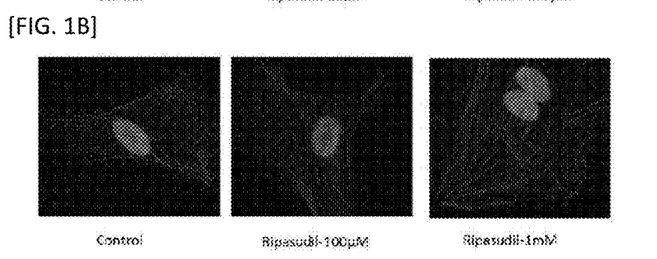
FIG. 1B is color photographs to observe the reversibility of the inhibition of actin stress fiber formation after removal of Ripasudil of the present invention, and the actin stress fibers are shown in red color.
Figure 2B:
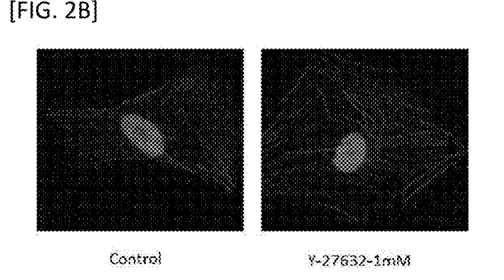
FIG. 2B is color photographs to observe the reversibility of the inhibition of actin stress fiber formation after removal of Y-27632, and the actin stress fibers are shown in red color.
Figure 3B:
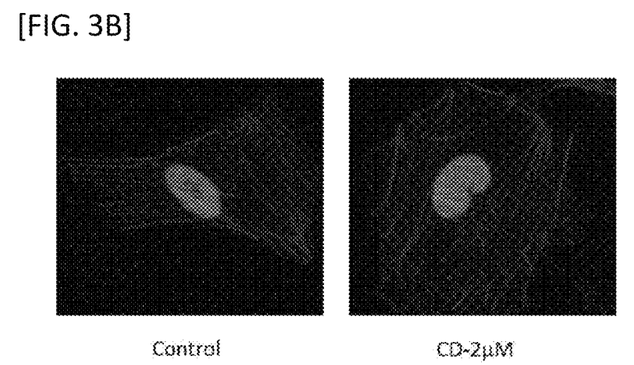
FIG. 3B is color photographs to observe the reversibility of the inhibition of actin stress fiber formation after removal of CD, and the actin stress fibers are shown in red color.

As the observation results, the test substance, Ripasudil, and the control are shown in FIG. 1B, the comparative control, Y-27632, and the control are shown in FIG. 2B, and the positive control and the control are shown in FIG. 3B using respective color photographs. The actin stress fibers are colored in red in the color photographs.

It is found that the actin stress fibers are recovered in the test substance, Ripasudil 100 μM and 1 mM (see FIG. 1B). Similarly, the actin stress fibers are also recovered in the comparative control, Y-27632 (see FIG. 2B). Further, the actin stress fibers are recovered in the positive control, CD (see FIG. 3B).

This showed that Ripasudil of the present invention had an inhibitory action on actin stress fiber formation but this action was reversible.

Example 3

Determination of G-Actin/F-Actin Ratio Using G-Actin/F-Actin In Vivo Assay Kit (Cytoskeleton, Inc.):

HLEpiC was diluted with a medium (Epithelial Cell Medium), and dispensed to a Poly-L-lysine coated T-75 flask at about 5000 cells/cm$^2$, and cultured in a carbon dioxide incubator (37° C., 5% $CO_2$) until about 50% confluent. A test substance, a positive control or the medium (control) at each concentration given below was added to each flask at 20 mL.

Test substance: Ripasudil with a concentration of 10 M, 100 μM or 1 mM,

Positive control: CD with a concentration of 2 μM, and

Control: only medium.

These were treated in a carbon dioxide incubator (37° C., 5% $CO_2$) for about an hour.

To 20 mL of Lysis and F-actin stabilization buffer was added 200 μL of 100 mM ATP stock solution and 200 μL of 100× Protease inhibitor cocktail stock to produce LAS2 buffer, and this was incubated in a carbon dioxide incubator (37° C.) for about 30 minutes. Warmed LAS2 buffer was added at 2.5 mL to each flask in which the medium was removed with vacuum suction.

Next, adherent HLEpiC was completely scraped with a cell scraper and transferred with the LAS2 buffer to a conical tube, and HLEpiC was crushed with a micropipette (hereinafter, referred to as cell solution). This cell solution was incubated in a carbon dioxide incubator (37° C.) for about 10 minutes and then centrifuged for 10 minutes (2000 rpm, room temperature). The supernatant was dispensed into an ultracentrifugal tube at 1.8 mL and centrifuged for an hour with an ultracentrifuge (100,000× g, 37° C.). At this time, F-actin is precipitated and G-actin remains in the supernatant.

The supernatant was transferred to a conical tube while being careful not to suck F-actin precipitates.

To precipitates of each sample was added 1.8 mL of F-actin depolymerizing buffer, and this was incubated under ice-cold conditions for an hour to depolymerize actin.

From each supernatant sample and precipitate sample, 100 μL each was put in a 1.5 mL Eppendorf tube, and 25 μL of 5×SDS sample buffer was added and stirred.

Each sample was boiled in a boiling water bath for 5 minutes.

Each sample was subjected to SDS-polyacrylamide gel electrophoresis, followed by Western blotting.

Next, after treatment using a Western blotting detection reagent (ECL Select Western Blotting Detection Reagent, GE Healthcare Japan), proteins were detected using a Lumino image analyzer. The quantities of G-actin and F-actin were determined using an analysis software (ImageQuant TL, GE Healthcare Japan) and the G-actin/F-actin ratio was calculated.

The results are shown in Table 1 given below.

TABLE 1

| Treatment | | G-actin/F-actin |
|---|---|---|
| Reagent | Concentration | ratio |
| Control | | 1.16 |
| Ripasudil | 10 μM | 1.91 |
| | 100 μM | 4.55 |
| | 1 mM | 24.87 |
| Cytochalasin D | 2 μM | 25.03 |

The variation in the quantity of F-actin required to form actin stress fibers was evaluated by comparison with the G-actin/F-actin ratio of untreated (Control) cells.

The G-actin/F-actin ratio of the control was 1.16. The G-actin/F-actin ratios of Ripasudil of the present invention at 10 μM, 100 μM and 1 mM were 1.91, 4.55 and 24.87 respectively, and when compared with the control, the value was slightly high in the 10 μM treatment and the values were obviously high in the 100 μM treatment or higher.

The G-actin/F-actin ratio of the positive control, CD 2 μM treatment, was 25.03, which was an obviously high value as compared to that of the control.

Example 4

Inhibitory Action on Cell Migration:

HLEpiC was diluted with a medium (Epithelial Cell Medium) and dispensed to Poly-L-lysine coated Oris™ Cell Migration 96 well plate, to which a stopper was firmly attached, at 50 μL/well (25000 cells/well) and cultured in a carbon dioxide incubator (37° C., 5% $CO_2$) for 24 hours. The stopper was removed, and after brief washing with the medium, a solution obtained by adding 5 μL of 10 mM Cell Tracker Green Fluorescent Probe (Lonza Walkersville, Inc.) to 4995 μL of the medium was added at 100 μL/well, and the cells were stained in a carbon dioxide incubator (37° C., 5% $CO_2$) for about 30 minutes. After brief washing with the medium, the medium was further added and the cells were cultured in a carbon dioxide incubator (37° C., 5% $CO_2$) for about 30 minutes.

After brief washing with the medium, a test substance, a positive control, a comparative control or the medium (control) at each concentration given below was added at 100 μL/well.

Test substance: Ripasudil with a concentration of 10 M, 100 μM or 1 mM,
Positive control: CD with a concentration of 2 μM,
Comparative control: Y-27632 with a concentration of 1 mM, and
Control: only medium.

These were cultured in a carbon dioxide incubator (37° C., 5% $CO_2$). The state of HLEpiC in the Detection Zone in each sample was observed by a confocal laser scanning microscope about 24 hours after the treatment and 48 hours after the treatment.

Figure 4:
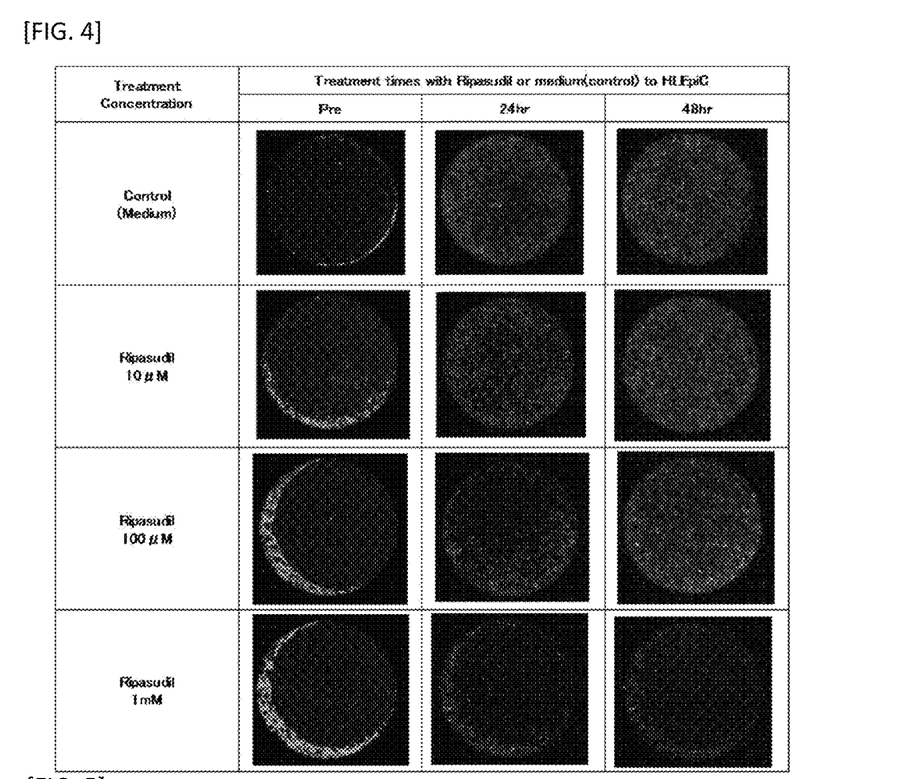
FIG. 4 is color photographs to observe the inhibitory action of Ripasudil of the present invention on HLEpiC migration, and green color represents cells.
Figure 5:
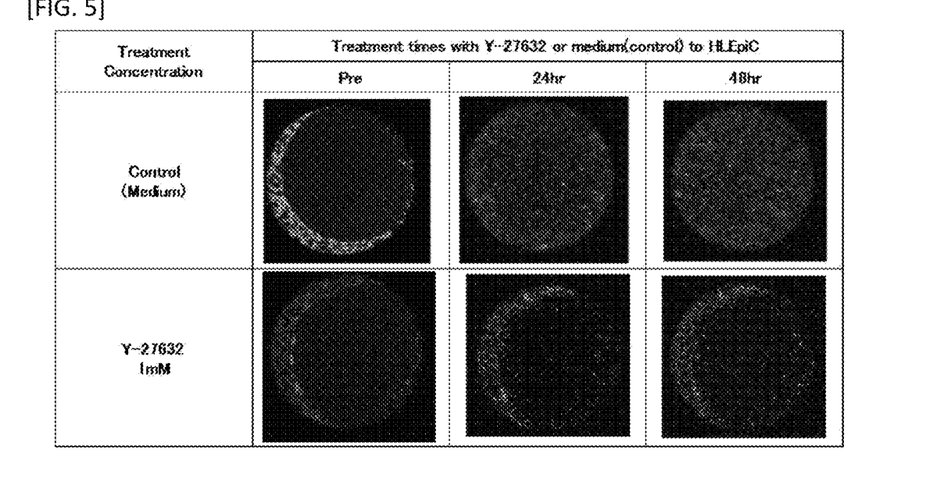
FIG. 5 is color photographs to observe the inhibitory action of Y-27632 used as a comparative control on lens epithelial cell migration, and green color represents cells.
Figure 6:
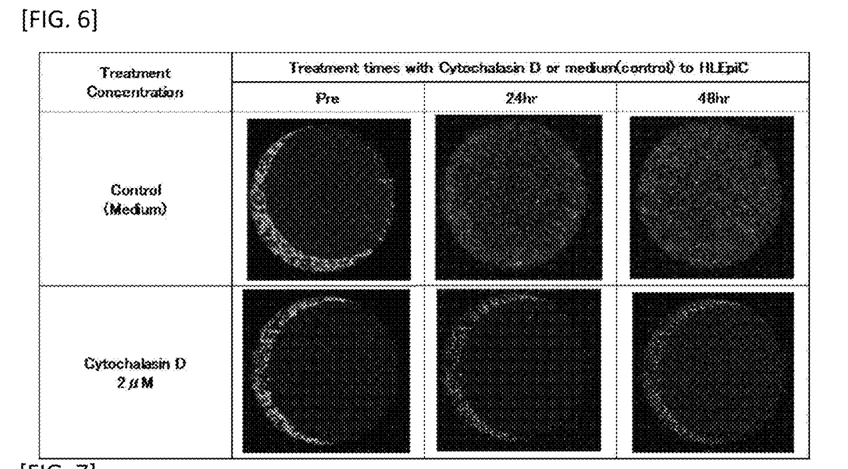
FIG. 6 is color photographs to observe the inhibitory action of CD used as a positive control on lens epithelial cell migration, and green color represents cells.

As the observation results, the test substance, Ripasudil, and the control are shown in FIG. 4, the comparative control, Y-27632, and the control are shown in FIG. 5, and the positive control and the control are shown in FIG. 6 using respective color photographs. The cells are colored in green in the color photographs.

A tendency of inhibition of cell migration was recognized in the test substance, Ripasudil 100 μM, and a definite inhibitory action on cell migration was recognized in 1 mM (see FIG. 4). Similarly, an inhibitory action on cell migration was also recognized in the comparative control, Y-27632 (see FIG. 5). Similarly, an inhibitory action on cell migration was further recognized in the positive control, CD (see FIG. 6).

This showed that Ripasudil of the present invention had an inhibitory action on cell migration of lens epithelial cells.

In addition, a whole image was also observed, and abnormalities in the state of HLEpiC were not recognized in the treatments with all reagents at all concentrations.

Example 5

Reversibility of Inhibition of Cell Migration:

After the operation in Example 4, the test substance, the positive control, or the comparative control was removed, and after brief washing with the medium, the medium was added at 100 μL/well, and the cells were cultured in a carbon dioxide incubator (37° C., 5% $CO_2$). The state of HLEpiC in the Detection Zone was observed about 24, 48 and further about 116 hours after removal by a confocal laser scanning microscope.

Figure 7:
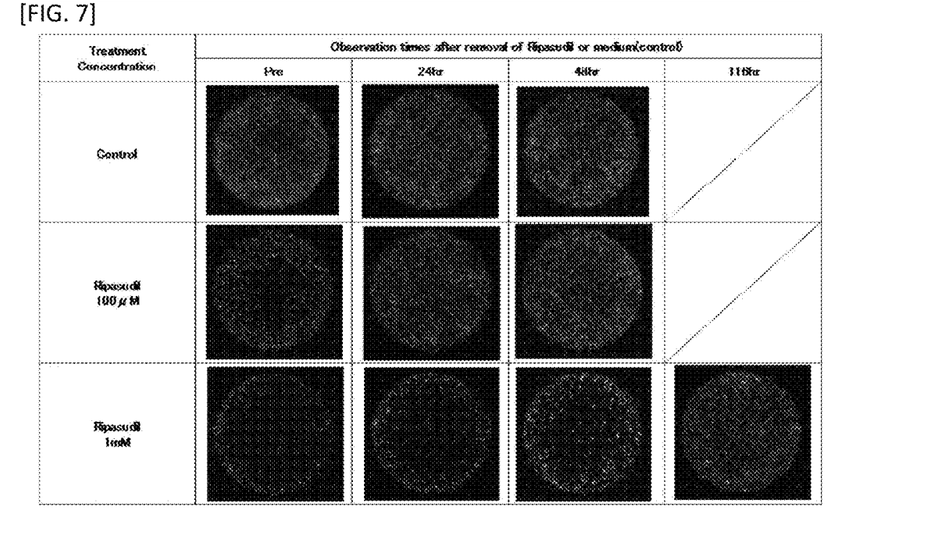
FIG. 7 is color photographs to observe the reversibility of the inhibition of HLEpiC migration after removal of Ripasudil of the present invention, and green color represents cells.
Figure 8:
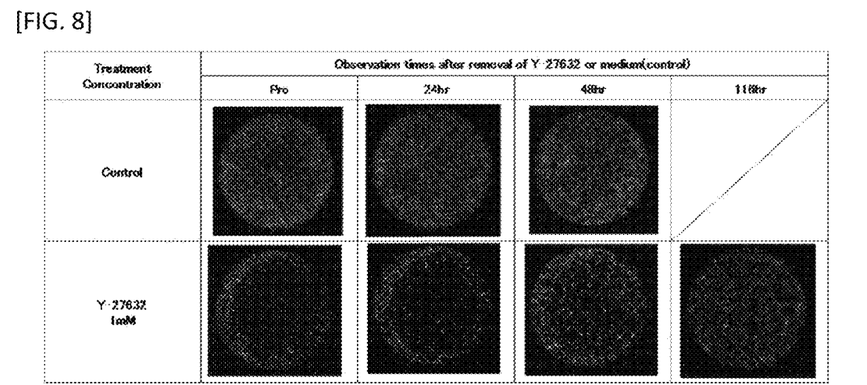
FIG. 8 is color photographs to observe the reversibility of the inhibition of HLEpiC migration after removal of Y-27632 used as a comparative control, and green color represents cells.
Figure 9:
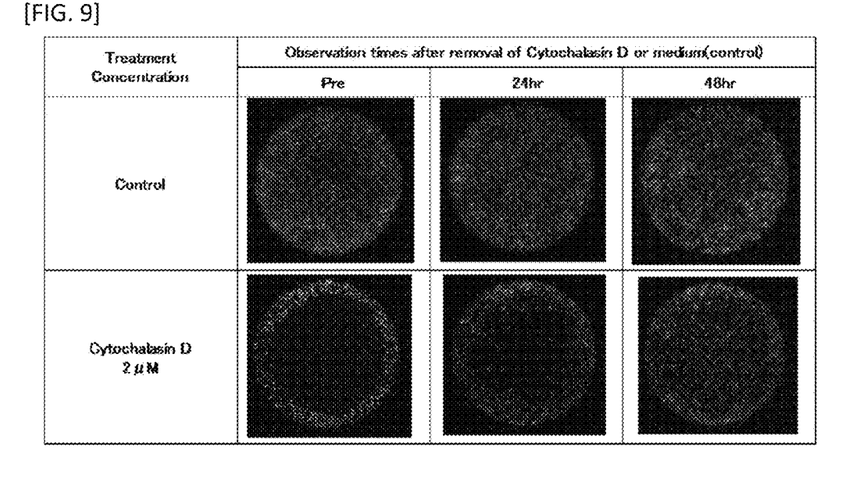
FIG. 9 is color photographs to observe the reversibility of the inhibition of lens epithelial cell migration after removal of CD used as a positive control, and green color represents cells.

As the observation results, the test substance, Ripasudil, and the control are shown in FIG. 7, the comparative control, Y-27632, and the control are shown in FIG. 8, and the positive control and the control are shown in FIG. 9 using respective color photographs. The cells are colored in green in the color photographs.

As compared to before removal, it was confirmed that HLEpiC migrated over time in the test substance, Ripasudil 100 μM treatment, and it was confirmed that the Detection zone was filled with HLEpiC about 24 hours after removal.

It was confirmed that HLEpiC gradually migrated over time in the 1 mM treatment; however, the Detection Zone was not filled with HLEpiC even about 48 hours after removal. It was confirmed, however, that HLEpiC migrated after 116 hours to the extent that the Detection Zone was filled. (see FIG. 7).

Similarly, it was also confirmed that HLEpiC gradually migrated over time in the comparative control, Y-27632; however, the Detection Zone was not filled with HLEpiC even about 48 hours after removal. It was confirmed, however, that HLEpiC migrated after 116 hours to the extent that the Detection Zone was filled (see FIG. 8).

Similarly, it was further confirmed that HLEpiC migrated over time in the positive control, CD, and it was confirmed that the Detection Zone was filled with HLEpiC about 48 hours after removal (see FIG. 9).

This showed that Ripasudil of the present invention had an inhibitory action on cell migration of lens epithelial cells but this action was reversible.

Example 6

Cytostatic Action

Normal human fibroblasts (Sanko Junyaku Co., Ltd.) were seeded at 2000 cells/well and cultured overnight. Next day, the medium (FGM-2 (Sanko Junyaku Co., Ltd.)) was exchanged (150 µL), and 10 µL of Ripasudil was then added so that the final concentration was 0.1 µM, 1 µM and 10 µM. After culturing for 2 days, 10 µL of BrdU (58.8-fold diluted solution: an undiluted solution is a 1000-fold solution) was added, and the cells were cultured for 2 hours. OD540-620 was measured using a plate reader after fixation and antibody addition, washing and coloring, and reaction termination in accordance with the protocol of Cell Proliferation ELISA BrdU kit (Roche), and an action on proliferation was evaluated. A value in a sample in which Ripasudil is not added is considered as 100%, and the uptake rate of BrdU under each condition is shown in Table 2.

TABLE 2

| Items | Ripasudil concentration (µM) | Uptake rate of BrdU (% of control) |
|---|---|---|
| Dermal fibroblast proliferation (Fibroblast) | 0.1 | 80.0 |
| | 1.0 | 59.3 |
| | 10.0 | 10.9 |

The uptake rates of BrdU were 80.0% in Ripasudil 0.1 M, 59.3% in 1 µM and 10.9% in 10 µM, and it was found that Ripasudil had a significant cytostatic action.

Example 7

Action of Ripasudil Hydrochloride Dihydrate on DNA Synthesis Capability of Human Lens Epithelial Cell Line (HLEs, SRA01/04)

Human lens epithelial cells (SRA01/04 (Riken Cell Bank)) were cultured using 20% FBS-DMEM medium under conditions of 37° C. and 5% $CO_2$.

The concentration of SRA01/04 was adjusted using 2% FBS-DMEM, and the cells were seeded in a 96 Well Plate at 100 µL/well (5000 cells/well) and cultured under conditions of 37° C. and 5% $CO_2$ for 24 hours. The medium was exchanged with 5% FBS-DMEM medium, and TGFβ at 10 ng/mL (final concentration) or Ripasudil at 10, 30 or 100 µM (final concentration) was added to each well, and the cells were cultured for another 24 hours. The uptake rate of 5-bromo-2'-deoxyuridine (BrdU) in the cells was measured using Cell Proliferation ELISA, BrdU (colorimetric) kit (Roche) at a measurement wavelength of 450 nm by Multiskan MS version 8.0 (LABSYSTEMS), and cell proliferation properties were evaluated.

Figure 10:
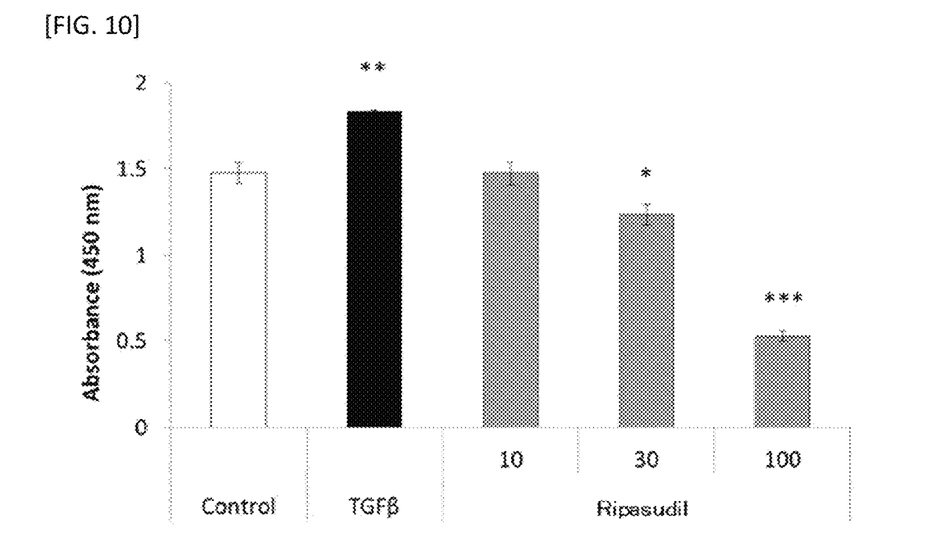
FIG. 10 shows the test results on the action of Ripasudil on cell proliferation (DNA synthesis capability) of human lens epithelial cells (SRA01/04). The results are shown by average±standard deviation, and significant differences are indicated by the * mark at p<0.05, the  mark at p<0.01 and the * mark at p<0.001.

The results are shown in FIG. 10. Consequently, it was confirmed that Ripasudil had a dose-dependent inhibitory action on DNA synthesis capability of human lens epithelial cells, and a statistically significant decrease was shown in 30 µM.

In addition, it is shown, in conjunction with the results in Example 6 mentioned above, that Ripasudil of the present invention has an inhibitory action on proliferation of cells including human lens epithelial cells.

Example 8

Action on Secondary Cataract Rabbit Model

Ten Japanese white rabbits (male) were used. After each rabbits were anesthetized, rabbits' left eye corneas were incised about 3 mm, and crystalline lens were removed with vacuum suction using ultrasonic emulsification aspirator. Intraocular lens were inserted into lens capsule from which the crystalline lens were removed. After the operation, necessary treatment using antimicrobial agents and anti-inflammatory agents were performed, and the progress was observed for three postoperative days.

After the postoperative observation, rabbits were divided into control group (five rabbits) and drug administered group (five rabbits) on the fourth postoperative day. To the drug administered group, Ripasudil 2% ophthalmic solution was administered four times a day, repeatedly for two weeks. To the control group, the corresponding placebo was administered.

Figure 11:
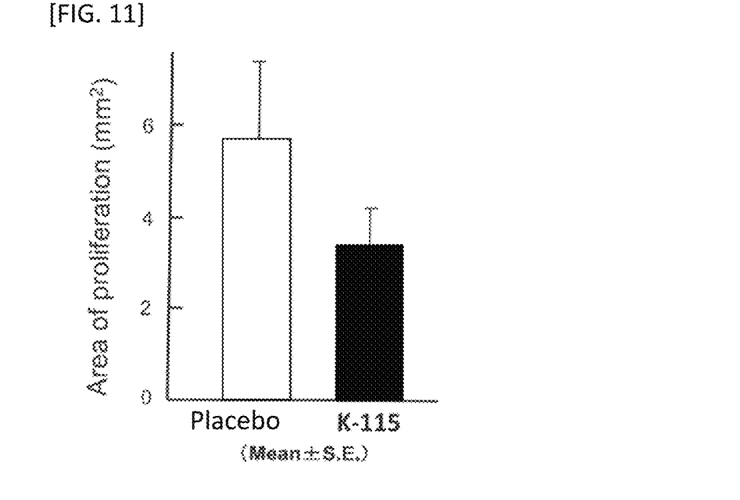
FIG. 11 is a chart showing the test results on the action of Ripasudil of the present invention on inhibition of lens epithelial cell proliferation in secondary cataract rabbit model. The vertical axis shows the proliferated area (mm$^2$), and the left side shows the control group (placebo) and the right side shows the drug administered group.

After two weeks from the start of the administration, rabbits' eyeballs were removed and paraffin-embedded. Embedded samples were sliced near the center of the eyeball by reference to the positions of optic nerve and iris, and the obtained thin slices were subjected to hematoxylin-eosin (H-E) staining and observed with a microscope. The area of tissue in which proliferation of lens epithelial cells was observed was measured by image analyzer, and the average was calculated. The results are shown in FIG. 11. The average of the control group (placebo) was 5.7 $mm^2$ while the average of the administered group was 3.3 $mm^2$, and it was confirmed that proliferation of lens epithelial cells was inhibited by the administration of Ripasudil 2% ophthalmic solution.

Example 9

Inhibitory Action on Collagen Gel Contraction

HT-1080 cell suspension adjusted to a density of 150000 to 200000 cells/mL with a medium (medium: E'MEM (Sigma)/10% FBS/NEAA/PCSM), and a solution, obtained by mixing A, B and C solutions (A solution: Cellmatrix (Collagen Type I 3 mg/mL), B solution: concentrated culture solution, 10×MEM Hank's culture solution, and C solution: buffer solution for reconstitution) of collagen gel culture kit (Nitta Gelatin Inc.) mixed at a ratio of 8:1:1 and cooling the obtained mixture, were mixed at a ratio of 1.4:1, and the obtained mixture was seeded in a 48 Well Plate at 500 µL/well and gelatinized in a $CO_2$ incubator to produce a cell-containing collagen gel. After gelation, 1 mL of the medium in which Ripasudil was adjusted to 0.1 µM, 1 µM or 10 µM was added on the gel, and an injection needle was inserted between the gel and the wall surface to release the gel from the wall surface, and the gel was incubated to stand in a $CO_2$ incubator. After two or three days, the contraction of the gel was observed, and photos were taken to evaluate the actions of Ripasudil.

When a contraction level was almost equal to that of a group to which Ripasudil was not added, (+) was used, (++) was used in the case where contraction was inhibited, and (+++) was used in the case where contraction was significantly inhibited.

The results are shown in Table 3 given below.

TABLE 3

| Items | Ripasudil concentration (μM) | Inhibition of contraction |
|---|---|---|
| Collagen contraction (HT1080) | 0.1 | + |
|  | 1.0 | ++ |
|  | 10.0 | +++ |

The action of Ripasudil on collagen gel contraction was (+) in 0.1 μM, (++) in 1 μM and (+++) in 10 μM, and it was found that Ripasudil had a dose-dependent inhibitory action on collagen gel contraction.

Ripasudil of the present invention or a salt thereof, or a solvate thereof is useful as medicines such as a preventive/therapeutic agent for complications after cataract surgery such as secondary cataract and anterior capsule contraction, an actin stress fiber formation inhibitor, a cell migration inhibitor, a cytostatic agent and a collagen gel contraction inhibitor, and has industrial applicability.

What is claimed is:

1. A method for preventing and/or treating complications after cataract surgery, comprising:
   administering to a subject with or at a risk of complications after cataract surgery a medicine comprising therapeutically and/or preventively effective amount of 4-fluoro-5-{[(2S)-2-methyl-1,4-diazepan-1-yl]sulfonyl}isoquinoline or a salt thereof, or a solvate thereof as an active ingredient,
   wherein the complications after cataract surgery is secondary cataract or anterior capsule contraction.

2. The method according to claim 1, wherein the solvate is a hydrate.

3. The method according to claim 1, wherein the complications after cataract surgery is secondary cataract.

4. The method according to claim 1, wherein the complications after cataract surgery is anterior capsule contraction.

5. The method according to claim 1, wherein the medicine is an ophthalmic solution.

6. The method according to claim 1, wherein the cataract surgery includes extracapsular lens extraction.

* * * * *